United States Patent
Sugizaki

(10) Patent No.: US 9,078,624 B2
(45) Date of Patent: Jul. 14, 2015

(54) RADIATION IMAGE DETECTING DEVICE, ELECTRONIC CASSETTE, AND RADIATION IMAGING SYSTEM

(71) Applicant: FUJIFILM Corporation, Tokyo (JP)

(72) Inventor: Makoto Sugizaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 267 days.

(21) Appl. No.: 13/721,742

(22) Filed: Dec. 20, 2012

(65) Prior Publication Data
US 2013/0208860 A1 Aug. 15, 2013

(30) Foreign Application Priority Data
Feb. 13, 2012 (JP) ................................. 2012-028436

(51) Int. Cl.
*A61B 6/00* (2006.01)
*G03B 42/02* (2006.01)
*G01N 23/04* (2006.01)
*G01T 1/29* (2006.01)

(52) U.S. Cl.
CPC ............... *A61B 6/542* (2013.01); *A61B 6/4233* (2013.01); *A61B 6/548* (2013.01); *G01T 1/2928* (2013.01); *G03B 42/02* (2013.01)

(58) Field of Classification Search
CPC ............ A61B 6/548; A61B 6/00; A61B 6/54; G03B 42/02; G01T 1/16; G01T 1/026; G01T 7/00
USPC ........ 378/62, 87, 98, 194; 250/354.1, 363.01, 250/370.09
See application file for complete search history.

(56) References Cited

U.S. PATENT DOCUMENTS

| 8,742,354 B2 * | 6/2014 | Shimizukawa et al. ..... 250/354.1 |
| 8,872,118 B2 * | 10/2014 | Nishino et al. ........... 250/370.09 |
| 2013/0075619 A1 * | 3/2013 | Sugizaki et al. .............. 250/394 |
| 2013/0077762 A1 * | 3/2013 | Noguchi et al. .............. 378/189 |
| 2013/0121471 A1 * | 5/2013 | Takahashi et al. .............. 378/98 |
| 2014/0291541 A1 * | 10/2014 | Watanabe et al. ............. 250/394 |

FOREIGN PATENT DOCUMENTS

| JP | 2002-590 A | 1/2002 |
| JP | 2008-154721 A | 7/2008 |

* cited by examiner

*Primary Examiner* — Nikita Wells
(74) *Attorney, Agent, or Firm* — Birch, Stewart, Kolasch & Birch, LLP

(57) ABSTRACT

An AEC signal is transmitted and received always in a wireless manner between a wireless communicator of an electronic cassette and a wireless communicator of a control device, regardless of the presence or absence of wired communication. If communication failure occurs in the wired communication and X-ray image data cannot be transmitted in a wired manner, a memory of the electronic cassette temporarily stores the X-ray image data. Since the AEC signal is wirelessly transmitted, X-ray imaging is continued even if the wired communication is unusable. A cause of the communication failure is more easily identified in wireless communication than in the wired communication. Thus, even if the communication failure occurs in the wireless communication, the wireless communication quickly recovers from the failure and downtime of an X-ray imaging system does not become too long.

11 Claims, 9 Drawing Sheets

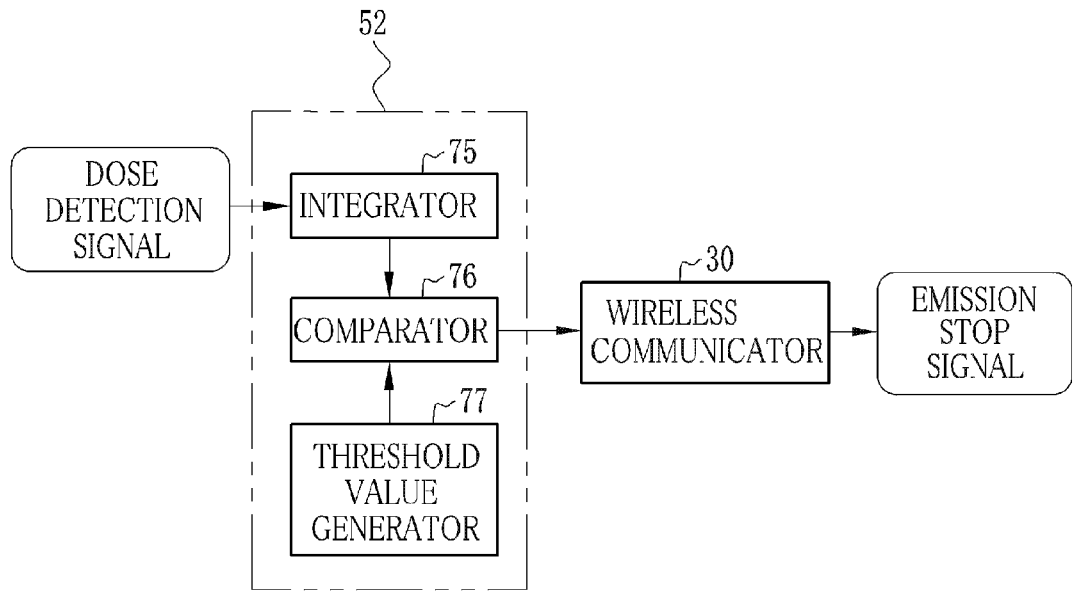

RADIATION IMAGE DETECTING DEVICE, ELECTRONIC CASSETTE, AND RADIATION IMAGING SYSTEM

BACKGROUND OF THE INVENTION

1. Field of the Invention

The present invention relates to a radiation image detecting device, an electronic cassette, and a radiation imaging system having an automatic exposure control function.

2. Description Related to the Prior Art

In a medical field, a radiation imaging system, for example, an X-ray imaging system using X-rays is widely known. The X-ray imaging system is constituted of an X-ray source for emitting the X-rays to an object, an X-ray image detecting device for detecting an X-ray image formed by the X-rays passed through the object, a control device for controlling the operation of the X-ray source and the X-ray image detecting device, and an emission switch for issuing an emission start command of the X-rays.

In the field of the X-ray imaging system, recently, the X-ray image detecting device that uses a flat panel detector (FPD) as a detection panel, instead of an X-ray film or an imaging plate (IP), becomes widespread. The FPD has a matrix of pixels each of which accumulates signal charge in accordance with an X-ray dose incident thereon. The FPD converts the signal charge accumulated in the individual pixels into a voltage signal, and outputs the X-ray image of the object as a time-series signal.

An electronic cassette (portable X-ray image detecting device) that has the FPD contained in a rectangular parallelepiped housing is in practical use. The electronic cassette is mounted for use not only on a specific imaging stand, but also on an existing imaging stand shareable with a film cassette and an IP cassette. Furthermore, the electronic cassette is sometimes used while being put on a bed under a patient's body or held by the patient himself/herself to take a radiograph of a body portion that is hard to handle with a stationary type of X-ray image detecting device. Also, the electronic cassette is sometimes brought out from a hospital for use in bedside radiography of a home-care patient or in an outside accident or natural disaster site having no imaging stand in case of emergency.

The X-ray image detected by the electronic cassette is transmitted to the control device, and written to a memory. This transmission is performed through wired communication. The imaging stand specific to the electronic cassette is provided with a connector in its cassette holder. By loading the electronic cassette in the imaging stand, a socket of the electronic cassette is connected to the connector. This connector is connected to the control device via a cable extending through the interior of the imaging stand. On the other hand, in the case of loading the electronic cassette in the existing imaging stand designed for the film cassette, or in the case of using the electronic cassette being put on the bed, the electronic cassette is connected to the control device through an external cable.

In the case of establishing the wired communication through the external cable connected between the electronic cassette and the control device, the cable becomes a nuisance. Thus, an electronic cassette having a wireless communication function is developed too. Wireless communication, however, is inferior to the wired communication in transmission speed. Worse yet, the wireless communication is in danger of causing interference from communication radio waves with other electronic equipment, so the electronic cassette having the wireless communication function is hard to use for the patient who has a pacemaker implanted in his/her heart. Therefore, as described in Japanese Patent Laid-Open Publication No. 2008-154721, an electronic cassette having both the wireless communication function and the wired communication function is developed.

The electronic cassette having both the wireless communication function and the wired communication function contains a battery used as a power source in the wireless communication. In the wired communication, the battery is recharged while the electronic cassette receives power supply from the control device. Since the wired communication is superior to the wireless communication in resistance to communication failure, the electronic cassette is automatically switched to the wired communication upon detecting the connection of the cable directly or through the cassette holder.

Also, the electronic cassette having an automatic exposure control (AEC) function is widely known. This electronic cassette is provided with a dose detection sensor for detecting the X-ray dose passed through the object. When an integral value of the detected X-ray dose i.e. an integral dose has reached a predetermined value, or when exposure time corresponding to the predetermined integral dose has elapsed, the X-ray emission from the X-ray source is stopped, and the FPD is shifted from a charge accumulation operation to a readout operation.

Japanese Patent Laid-Open Publication No. 2002-000590 describes an X-ray image detecting device that uses some of the pixels as the dose detection sensors. In this device, the X-ray dose is measured based on a signal from the dose detection sensor, and a signal (emission stop signal) for commanding the stop of X-ray emission is issued. The emission stop signal is transmitted to the control device through the wired communication.

The wired communication has various merits, as described above. However, in case of the communication failure, the wired communication requires a long time to find out a cause due to many relay parts including the cable and connectors. To be more specific, a cable break, a connector contact failure, a breakdown in a relay device such as a hub, a breakdown in another device connected through a network, and the like are conceivable as the cause of the wired communication failure. In the occurrence of the communication failure, the cable break, the connector contact failure, and the operation of the relay device are checked to identify the cause, and it requires a long time. Furthermore, after the identification of the cause, a broken part needs replacing and a replaced new part needs operation check, so it requires a longer time.

In the Japanese Patent Laid-Open Publication Nos. 2002-000590 and 2008-154721, an AEC signal is transmitted through the wired communication. In such systems, recovery in the communication of the AEC signal is absolutely necessary for radiography, and delay in the recovery elongates downtime of the system. However, neither of the Japanese Patent Laid-Open Publication Nos. 2002-000590 and 2008-154721 describes an object of rapidly recovering from the communication failure of the AEC signal and a solution thereof.

SUMMARY OF THE INVENTION

An object of the present invention is to provide a radiation image detecting device, an electronic cassette, and a radiation imaging system that can rapidly deal with communication failure of a signal for use in automatic exposure control.

To achieve the above and other objects, a radiation image detecting device according to the present invention includes an imaging section, a dose detection sensor, an automatic exposure control unit, a wired communicator, and a wireless communicator. The imaging section has pixels arranged in two dimensions. Each of the pixels converts radiation emitted from a radiation source into electric charge, and accumulates the electric charge. A radiographic image is obtained by reading out the electric charge from the pixels. The dose detection sensor detects a received dose of the radiation. The automatic exposure control unit issues an emission continuation signal for commanding continuation of radiation emission or an emission stop signal for commanding stop of the radiation emission based on a dose detection signal from the dose detection sensor. The wired communicator transmits and receives a signal to and from a control device in a wired manner. The wired communicator is actuated in response to cable connection between the control device and the radiation image detecting device. The wireless communicator transmits and receives the signal to and from the control device in a wireless manner. The wireless communicator is in charge of transmission of at least the emission continuation signal or the emission stop signal, regardless of the presence or absence of the cable connection.

The radiographic image is transmitted to the control device, and the wired communicator is preferably in charge of the transmission of the radiographic image. The radiation image detecting device is preferably provided with a memory that stores the radiographic image to be transmitted to the control device, if communication failure occurs between the wired communicator and the control device.

When the wired communicator receives an emission start signal of the radiation from the control device through a cable, each of the pixels preferably starts accumulating the electric charge.

The radiation image detecting device preferably includes the control unit that performs a judging step and a charge accumulation starting step. In the judging step, if the communication failure occurs between the wired communicator and the control device connected each other through the cable, the start of the radiation emission from the radiation source is judged based on the dose detection signal from the dose detection sensor. In the charge accumulation starting step, upon judgment of the start of the radiation emission, each of the pixels starts accumulating the electric charge.

The wireless communicator preferably transmits and receives the signal through ad-hoc communication. The wireless communicator preferably transmits and receives the signal through a beacon. The dose detection sensor is preferably arranged together with the pixels in two dimensions.

An electronic cassette is constituted of the radiation image detecting device and a portable housing containing the radiation image detecting device. When the electronic cassette is loaded in an imaging stand, the wired communicator is preferably connected to the control device through a cable extending through an interior of the imaging stand.

A radiation imaging system includes the radiation source, the control device, and the radiation image detecting device. The control device controls the radiation source and the radiation image detecting device. The control device has a first wired communicator and a first wireless communicator. The radiation image detecting device includes the imaging section, the dose detection sensor, the automatic exposure control unit, a second wired communicator, and a second wireless communicator. The imaging section has the pixels arranged in two dimensions. Each of the pixels converts the radiation emitted from the radiation source into the electric charge and accumulates the electric charge. The radiographic image is obtained by reading out the electric charge from the pixels. The dose detection sensor detects the received dose of the radiation. The automatic exposure control unit issues the emission continuation signal for commanding continuation of the radiation emission or the emission stop signal for commanding stop of the radiation emission based on the dose detection signal from the dose detection sensor. The second wired communicator is actuated when being connected to the first wired communicator through a cable, for performing transmission and reception of a signal in a wired manner. The second wireless communicator transmits and receives the signal to and from the first wireless communicator in a wireless manner. The second wireless communicator is in charge of transmission of at least the emission continuation signal or the emission stop signal, regardless of the presence or absence of connection of the cable.

According to the present invention, the signal for use in automatic exposure control is transmitted and received in a wireless manner. A cause of the communication failure is more easily identified in wireless communication than in the wired communication. Thus, it is possible to deal with the communication failure more quickly in the wireless communication than in the wired communication. Since the signal for use in the automatic exposure control, which is absolutely necessary for radiation imaging, is transmitted and received through the wireless communication, it is possible to shorten downtime of the radiation imaging system.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 5 is a block diagram showing the structure of an AEC unit;

FIG. 6 is a table of exposure conditions;

DESCRIPTION OF THE PREFERRED EMBODIMENTS

Figure 1:
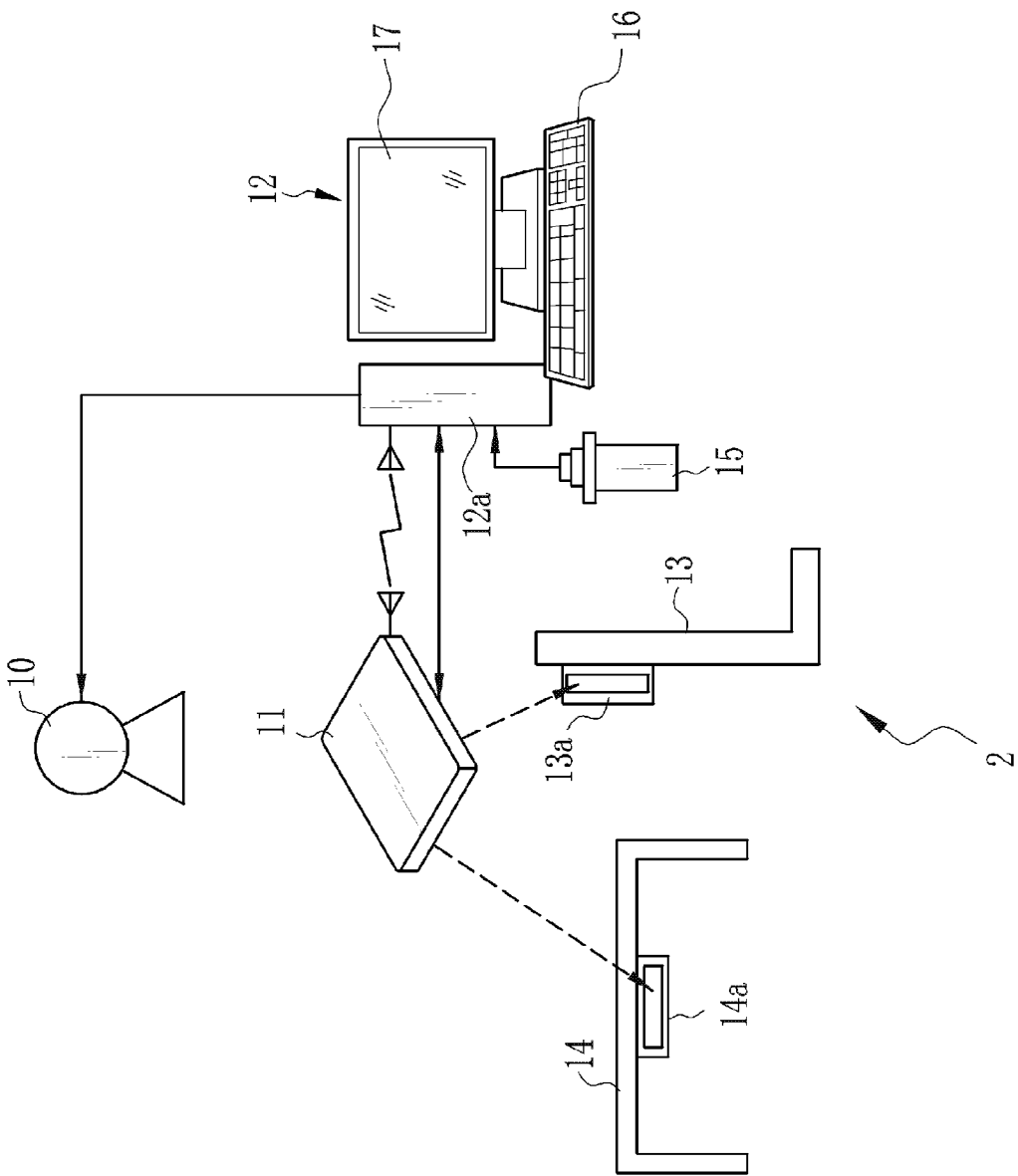
FIG. 1 is a schematic view of an X-ray imaging system.

As shown in FIG. 1, an X-ray imaging system 2 is constituted of an X-ray source 10 containing an X-ray tube for emitting X-rays, a radiation image detecting device e.g. an electronic cassette 11 that detects the X-rays passed through an object and outputs an X-ray image, a control device 12 for controlling the operation of the X-ray source 10 and the electronic cassette 11, an imaging stand 13 used in imaging a patient in a standing position, and an imaging table 14 used in imaging the patient in a lying position. The imaging stand 13 has a cassette holder 13a, and the imaging table 14 has a cassette holder 14a into which the electronic cassette 11 is loaded. In addition, the X-ray imaging system 2 has a source shift mechanism (not shown) for setting the X-ray source 10 in a desired orientation and position. The control device 12 includes a main unit 12a, an input device 16, and a monitor 17.

The X-ray source 10 has the X-ray tube for emitting the X-rays, and a collimator for limiting an irradiation field of the X-rays. The X-ray tube has a cathode being a filament for emitting thermoelectrons, and an anode (target) for radiating the X-rays by collision of the thermoelectrons emitted from the cathode. The collimator is composed of, for example, four X-ray shielding lead plates disposed on each side of a rectangle so as to form an irradiation opening in its middle through which the X-rays propagate. Changing the positions of the lead plates varies the size of the irradiation opening to determine the irradiation field.

Figure 2:
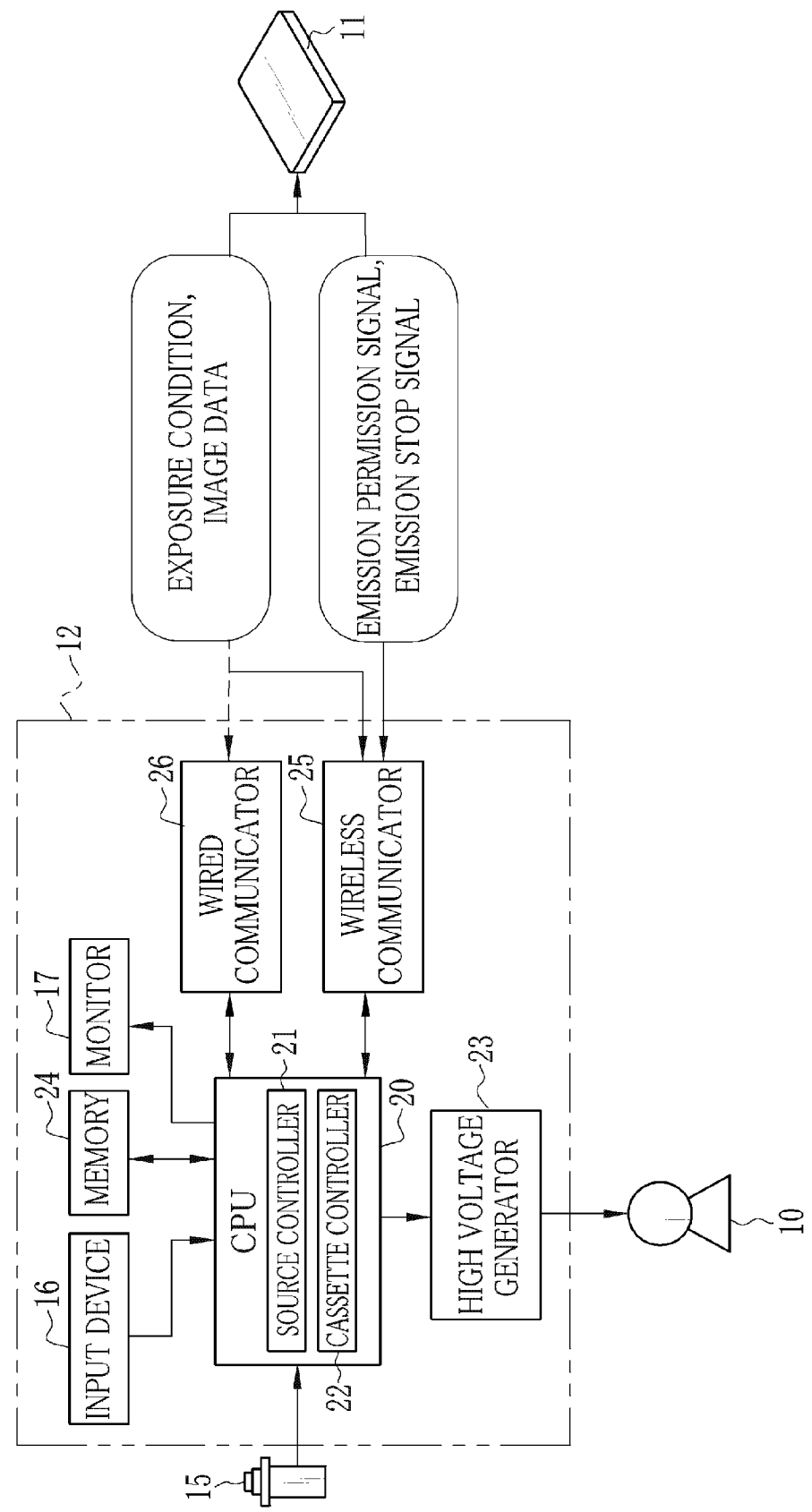
FIG. 2 is a block diagram showing the structure of a control device.

As shown in FIG. 2, the control device 12 has a CPU 20 contained in the main unit 12a. This CPU 20 functions as a source controller 21 and a cassette controller 22. To the CPU 20, an emission switch 15, the input device 16, the monitor 17 for displaying an operation screen and the X-ray image, a high voltage generator 23, a memory 24 for storing X-ray image data, and the like are connected. After completion of the imaging, the X-ray image data stored in the memory 24 is written to an image server (not shown) connected to the control device 12 through a network.

The high voltage generator 23 multiplies an input voltage into a high tube voltage by a transformer, and supplies the high tube voltage to the X-ray source 10 through a high voltage cable. The source controller 21 controls the tube voltage for determining an energy spectrum of the X-rays emitted from the X-ray source 10, a tube current for determining an X-ray irradiation amount per unit of time, and an X-ray irradiation time.

The emission switch 15 is, for example, a two-step press switch operated by a radiological technician. Upon a half press of the emission switch 15, a warm-up start signal is issued to start warming up the X-ray source 10. Upon a full press of the emission switch 15, an emission start signal is issued to start emitting the X-rays from the X-ray source 10. These signals are inputted to the source controller 21 through a signal cable. In response to the emission start signal from the emission switch 15, the source controller 21 starts electric power supply from the high voltage generator 23 to the X-ray source 10 to produce the X-rays.

The memory 24 stores in advance several types of exposure conditions each including the tube voltage, the tube current, and the like. The radiological technician manually chooses through the input device 16 an appropriate exposure condition out of the several types of exposure conditions in accordance with a body portion to be imaged. Based on the chosen exposure condition, the tube voltage, the tube current, and a tube current-time product are set up in the source controller 21. The tube current-time product (or the X-ray irradiation time) is set at such a value that can produce the X-ray image adequate for diagnosis and cannot apply an excessive radiation dose to the detriment of the patient's health, even if an AEC unit 52 (see FIGS. 3 and 5) of the electronic cassette 13 malfunctions. The source controller 21 starts X-ray emission with the set tube voltage, the set tube current, and the set tube current-time product. During the X-ray emission, the AEC unit 52 detects an integral dose applied to the object. When application of an enough dose is detected, the AEC unit 52 stops the X-ray emission.

The control device 12 is provided with a wireless communicator 25 and a wired communicator 26. The wireless communicator 25 transmits and receives various signals (hereinafter collectively called AEC signal) for use in AEC to and from the electronic cassette 11. To be more specific, upon receiving the warm-up start signal from the emission switch 15, the source controller 21 transmits an inquiry signal to the electronic cassette 11 through the wireless communicator 25. Upon receiving the inquiry signal, the electronic cassette 11 checks whether or not the electronic cassette 11 itself is ready for imaging. If the electronic cassette 11 is ready, the electronic cassette 11 transmits an emission permission signal. In response to receiving the emission permission signal at the wireless communicator 25 and receiving the emission start signal from the emission switch 15, the source controller 21 starts electric power supply from the high voltage generator 23 to the X-ray source 10. This emission start signal is wirelessly transmitted to the electronic cassette 11 via the control device 12. The source controller 21 receives an emission stop signal issued from the electronic cassette 11 at its wireless communicator 25. Upon receiving the emission stop signal, the source controller 21 stops the electric power supply from the high voltage generator 23 to the X-ray source 10 to stop the X-ray emission.

Not only the AEC signal but also other signals including the exposure condition and the X-ray image data are wirelessly transmitted and received between the wireless communicator 25 and the electronic cassette 11. The wired communicator 26 is connected to the electronic cassette 11 with a cable in a case where the exposure condition, the X-ray image data, and the like cannot be transmitted wirelessly. The wired communicator 26 has a power feeding function, and supplies drive power to the electronic cassette 11 connected thereto with the cable.

The cassette controller 22 controls the operation of the electronic cassette 11 in response to input operation by the radiological technician through the input device 16. More specifically, the cassette controller 22 controls the power on and off, the mode switching between a standby mode and an imaging mode, and the like of the electronic cassette 11.

The control device 12 receives input of an examination order including information about the sex and age of the patient, the body portion to be imaged, an examination purpose, and the like, and displays the examination order on the monitor 17. The examination order is inputted from an external system e.g. HIS (hospital information system) or RIS (radiography information system) that manages patient data and examination data related to radiography, or inputted manually by the radiological technician from the input device 16. The examination order includes the body portion to be imaged e.g. head, chest, and abdomen, and an imaging direction e.g. anterior, medial, diagonal, PA (X-rays are applied from a posterior direction), and AP (X-rays are applied from an anterior direction). The radiological technician checks the contents of the examination order on the monitor 17, and inputs the exposure condition corresponding to the contents of the examination order through the operation screen displayed on the monitor 17.

Figure 3:
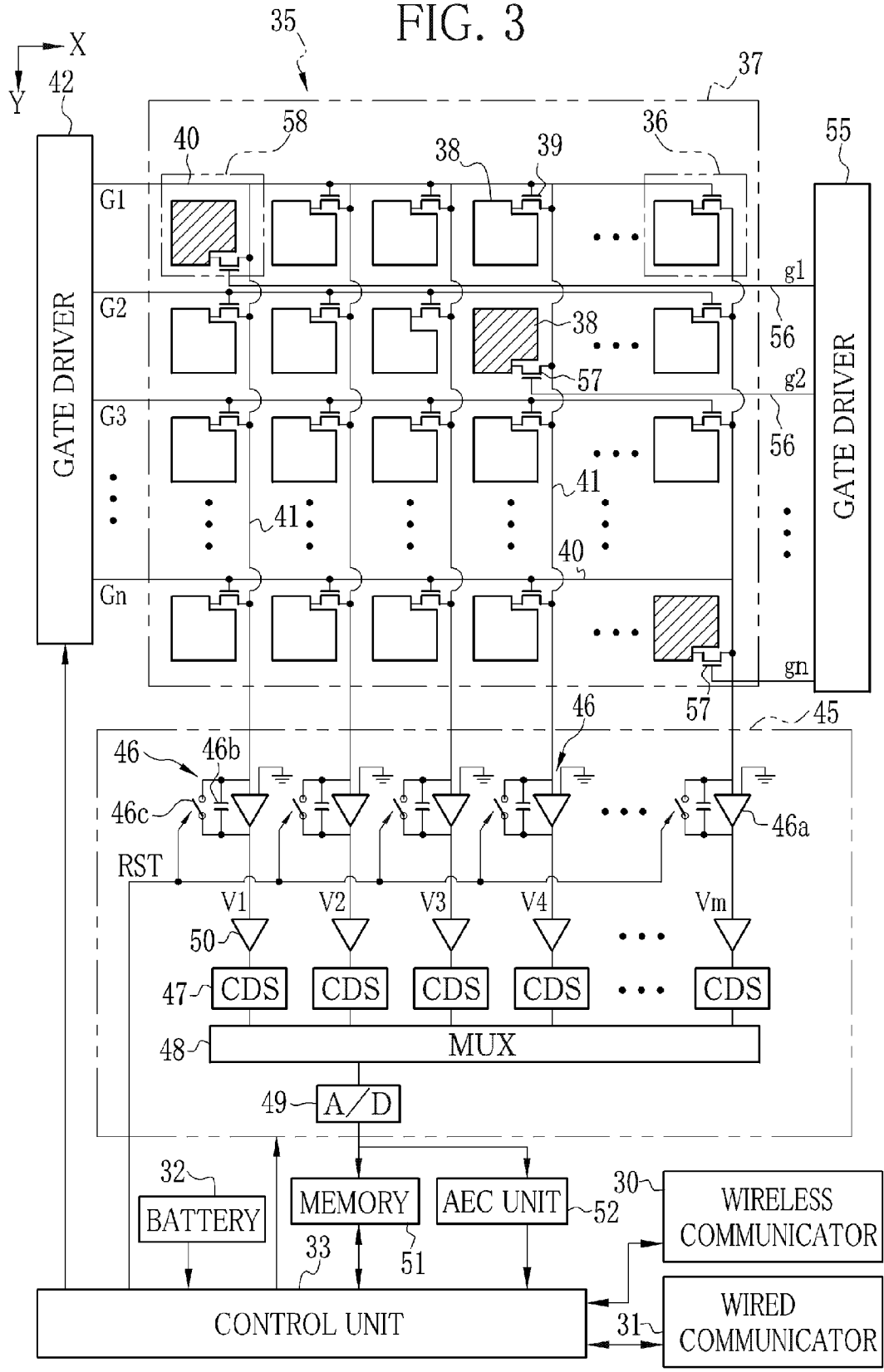
FIG. 3 is a block diagram showing the structure of an electronic cassette.

In FIG. 3, the electronic cassette 11 includes an FPD 35, a circuit board on which a control unit 33 and the like are mounted, a battery 32, and a portable housing containing these components. The housing of the electronic cassette 11 is in a rectangular flat box shape, as is widely known, and is compatible with the ISO 4090:2001 in size, as with a film cassette and an IP cassette (also called CR cassette). Thus, the electronic cassette 11 is loadable into an existing imaging stand designed for the film cassette and the IP cassette.

The electronic cassette 11 is detachably set on the cassette holder 13a or 14a of the imaging stand 13 or the imaging table 14 in such a position that an imaging section 37 of the FPD 35 is opposed to the X-ray source 10. Since both the imaging stand 13 and the imaging table 14 are installed in an examination room, a plurality of electronic cassettes 11 are generally provided in the single examination room. In addition, the electronic cassette 11 is sometimes used independently of the imaging stand 13 or the imaging table 14 in a state of being put on a bed on which the patient is lying, or being held by the patient himself/herself.

The electronic cassette 11 contains a wireless communicator 30 for establishing wireless communication with the control device 12, a wired communicator 31 for establishing wired communication with the control device 12, the battery 32, and the like. The wireless communicator 30 and the wired communicator 31 mediate transmission and reception of various types of information and signals including the X-ray image data between the control device 12 and the control unit 33. Specifically, the wireless communicator 30 transmits and receives the AEC signal to and from the wireless communicator 25 of the control device 12. The battery 32 supplies operation power to the electronic cassette 11, in the case of the wireless communication. The battery 32 is small enough to be contained within the slim electronic cassette 11. The battery 32 is taken out of the electronic cassette 11 and mounted on a specific cradle for recharging. Alternatively, the battery 32 may be recharged by a wireless power feeder. The control unit 33, a memory 51, the wireless communicator 30, the wired communicator 31, and the like are mounted on the circuit board (not shown).

The wired communicator 31 is used in case that, for example, the wireless communication fails between the electronic cassette 11 and the control device 12 because of low battery power. The wired communicator 31 is connected to the wired communicator 26 of the control device 12 with the cable. When the cable extending from the control device 12 is connected to the wired communicator 31, the control device 12 detects this cable connection, and deactuates the wireless communicator 30 and actuates the wired communicator 31. The control device 12 feeds power to the electronic cassette 11, while the battery 32 stops feeding power thereto. The battery 32 may be recharged with the electric power from the control device 12 through the wired communicator 31. The cable connection may be detected by the electrical conduction between a connector and a cable socket or by a sensor switch for detecting connection to the connector.

The FPD 35 is provided with the imaging section 37, which has a TFT active matrix substrate and a plurality of pixels (including normal pixels 36 and detection pixels 40) arranged on the substrate. Each pixel accumulates electric charge in accordance with the X-ray dose incident thereon. The pixels are arranged into a two-dimensional matrix with n rows (X direction) and m columns (Y direction) at a predetermined pitch.

The FPD 35 is of an indirect conversion type, having a scintillator (phosphor) for converting the X-rays into visible light. The pixels perform photoelectric conversion of the visible light produced by the scintillator. The scintillator is made of CsI:Tl (thallium activated cesium iodide), GOS ($Gd_2O_2S$: Tb, gadolinium oxysulfide), or the like. The scintillator is opposed to the imaging section 37 having the pixels. The scintillator and the TFT active matrix substrate may adopt either a PSS (penetration side sampling) method or an ISS (irradiation side sampling) method. In the PSS method, the scintillator and the TFT active matrix substrate are disposed in this order from an X-ray incident side, while being disposed in reverse order in the ISS method. Note that, a direct conversion type FPD, which has a conversion layer (amorphous selenium or the like) for directly converting the X-rays into the electric charge without having the scintillator, may be used instead. Furthermore, a CMOS method may be adopted instead of a TFT method.

As is widely known, the normal pixel 36 is composed of a photodiode 38 being a photoelectric conversion element that produces the electric charge (electron and hole pairs) by entry of the visible light, a capacitor (not shown) for accumulating the produced electric charge, and a thin film transistor (TFT) 39 being a first switching element. Without providing the capacitor, the electric charge may be accumulated in the photodiode 38.

The photodiode 38 is composed of a semiconducting layer (of PIN type, for example) for producing the electric charge, and upper and lower electrodes disposed on the top and bottom of the semiconducting layer. The lower electrode of the photodiode 38 is connected to the TFT 39. The upper electrode of the photodiode 38 is connected to a bias line. The number of the bias lines coincides with the number of the rows ("n" rows) of the pixels in the imaging section 37. All the "n" bias lines are connected to a bias power source through a bus. The bias power source applies bias voltage to the upper electrodes of the photodiodes 38 through the bus and the bias lines. Since the application of the bias voltage produces an electric field in the semiconducting layer, the electric charge (electron and hole pairs) produced in the semiconducting layer by the photoelectric conversion is attracted to the upper and lower electrodes, one of which has positive polarity and the other has negative polarity. Thereby, the electric charge is accumulated in the capacitor.

A gate electrode of the TFT 39 is connected to a scan line 40. A source electrode of the TFT 39 is connected to a signal line 41. A drain electrode of the TFT 39 is connected to the photodiode 38. The scan lines 40 and the signal lines 41 are routed into a lattice. The number of the scan lines 40 coincides with the number "n" of the rows of the pixels in the imaging section 37. The number of the signal lines 41 coincides with the number "m" of the columns of the pixels. Every scan line 40 is connected to a gate driver 42, and every signal line 41 is connected to a signal processing circuit 45.

The gate driver 42 drives the TFTs 39 so that the FPD 30 performs a charge accumulation operation in which the normal pixels 36 accumulate the signal charge in accordance with the received X-ray dose, a readout (actual readout) operation in which the accumulated signal charge is read out from the normal pixels 36, and a reset (idle readout) operation. The control unit 33 controls the start timing of each above operation performed by the gate driver 42.

In the charge accumulation operation, while every TFT 39 is turned off, every normal pixel 36 accumulates the signal charge produced therein. In the readout operation, the gate driver 42 sequentially issues gate pulses G1 to Gn each of which drives the TFTs 39 of the same row at a time. Thereby, the scan lines 40 are activated one by one, and the TFTs 39 connected to the activated scan line 40 are turned on row by row. Upon turning on the TFT 39, the signal charge accumulated in the capacitor of the normal pixel 36 is read out to the signal line 41, and inputted to the signal processing circuit 45.

The signal processing circuit 45 is provided with integrating amplifiers 46, CDS circuits (CDSs) 47, a multiplexer (MUX) 48, an A/D converter (A/D) 49, and the like. One integrating amplifier 46 is connected to each signal line 41. The integrating amplifier 46 includes an operational amplifier 46a and a capacitor 46b connected between input and output terminals of the operational amplifier 46a. The signal line 41 is connected to one of two input terminals of the operational amplifier 46a. The other input terminal of the operational amplifier 46a is connected to a ground (GND). To the capacitor 46b, a reset switch 46c is connected in parallel. While the reset switch 46c is turned off, the integrating amplifier 46 converts the electric charge inputted from the signal line 41 into an analog voltage signal V1 to Vm by integration. An output terminal of every operational amplifier 46a is connected to the MUX 48 through another amplifier 50 and the CDS 47.

The CDS 47 applies correlated double sampling to the output voltage signal from the integrating amplifier 46 to remove noise, and holds the output voltage signal from the integrating amplifier 46 for a predetermined period in its sample hold circuits. The MUX 48 sequentially selects one of the CDSs 47 connected in parallel to one another by an electronic switch based on an operation control signal from a shift resister (not shown), so the voltage signals V1 to Vm outputted from the CDSs 47 are inputted to the A/D 49 in series. The A/D 49 converts the inputted voltage signals V1 to Vm into a digital voltage signal, and outputs the digital voltage signal to the memory 51 or the AEC unit 52 contained in the electronic cassette 11. Another amplifier may be connected between the MUX 48 and the A/D 49. The A/D may be provided in each signal line 41. In such a case, the MUX is disposed behind the A/Ds.

After the MUX 48 reads out the voltage signals V1 to Vm of one row from the integrating amplifiers 46, the control unit 33 outputs a reset pulse RST to the integrating amplifiers 46, so every reset switch 46c is turned on. Thereby, the signal charge of one row accumulated in the capacitors 46b is discharged and reset. After the reset of the integrating amplifiers 46, the reset switches 46c are turned off again. After a lapse of predetermined time from the turn off of the reset switch 46c, one of the sample hold circuits of each CDS 50 holds and samples a kTC noise component of each integrating amplifier 46. After that, the gate driver 42 outputs the gate pulse of the next row to start reading out the signal charge from the normal pixels 36 of the next row. After a lapse of predetermined time from the output of the gate pulse, the other sample hold circuit of each CDS 47 holds the signal charge from the normal pixel 36 of the next row. By repetition of the above operations, the signal charge is read out from the pixels 36 of every row. The above operations may be concurrently performed by pipeline processing for speeding up.

After the completion of the readout from every row, the image data representing the X-ray image of a single frame is stored in the memory 51. This image data is immediately read out from the memory 51, and outputted to the control device 12 through the wireless communicator 30 or the wired communicator 31. Thereby, the X-ray image of the object is detected.

The memory 51 has a capacity of the X-ray image data of a plurality of frames, for example, a hundred frames. In case where communication failure disables the transmission of the X-ray image data from the wireless communicator 30 or the wired communicator 31, the memory 51 temporarily stores the X-ray image data outputted from the FPD 35 during that time. The X-ray image data that is temporarily stored in the memory 51 is transmitted at a time or over several times, after recovery from the communication failure. An additional memory that temporarily stores the X-ray image data in case of the communication failure may be provided in addition to the memory 51. This additional memory may be a removable medium, which is detachable from the electronic cassette 11. In case of the communication failure, the removable medium may be detached from the electronic cassette 11 and connected to the control device 12 to directly readout the X-ray image data.

During the operation of the FPD 35, dark charge occurs in the semiconducting layer of the photodiode 38 regardless of the presence or absence of entry of the X-rays, and is accumulated in the capacitor of the normal pixel 36. The dark charge occurring in the normal pixels 36 becomes noise of the image data, and therefore the reset operation is carried out at predetermined intervals to remove the dark charge. The reset operation is an operation in which the dark charge occurring in the normal pixels 36 is discharged through the signal lines 41.

The reset operation adopts a sequential reset method, for example, in which the normal pixels 36 are reset on a row-by-row basis. In the sequential reset method, as in the case of the readout operation of the signal charge, the gate driver 42 sequentially issues the gate pulses G1 to Gn to the scan lines 40, to turn on the TFTs 39 of the normal pixels 36 on a row-by-row basis. While the TFT 39 is turned on, the dark charge flows from the normal pixel 36 through the signal line 41 to the capacitor 46b of the integrating amplifier 46. In the reset operation, in contrast to the readout operation, the MUX 48 does not read out the electric charge accumulated in the capacitors 46b. The control unit 33 issues the reset pulse RST in synchronization with the issue of each of the gate pulses G1 to Gn. Thereby, the reset switch 46c is turned on, and the electric charge accumulated in the capacitor 46b is discharged to reset the integrating amplifier 46.

Instead of the sequential reset method, a parallel reset method or an all pixels reset method may be used. In the parallel reset method, a plurality of rows of pixels are grouped together, and sequential reset is carried out in each group so as to concurrently discharge the dark charge from the rows of the number of the groups. In the all pixels reset method, the gate pulse is inputted to every row to concurrently discharge the dark charge from every pixel. Using the parallel reset method and the all pixels reset method can reduce time required for the reset operation.

The FPD 35 includes a plurality of detection pixels 58, besides the normal pixels 36, disposed in the same imaging section 37. The detection pixel 58 is provided with a TFT 57 driven by a gate driver 55 and a scan line 56 that are different from the gate driver 42 and the scan line 40 of the normal pixel 36. The TFTs 57 are turned on by gate pulses g1 to gn from the gate driver 55. The detection pixel 58 has exactly the same fundamental structure of the photodiode 38 and the like as that of the normal pixel 36, except for a drive source. Accumulated electric charge from the detection pixel 58 is read out to the signal line 41 independently of that from the normal pixel 36. After the completion of the reset operation or the readout operation of the normal pixels 36, the gate driver 55 issues the gate pulses g1 to gn to perform the reset operation and the readout operation of the detection pixels 58 in a like manner. Alternatively, both the normal pixels 36 and the detection pixel 58 of the same row perform the reset operation or the readout operation at the same time by synchronizing the operation of the gate driver 42 and the gate driver 55. The detection pixels 58 are used for detecting the X-ray dose received by the imaging section 37, and function as AEC sensors. The number of the detection pixels 58 is of the order of a few ppm to a few percent of the number of the all pixels arranged in the imaging section 37.

Figure 4:
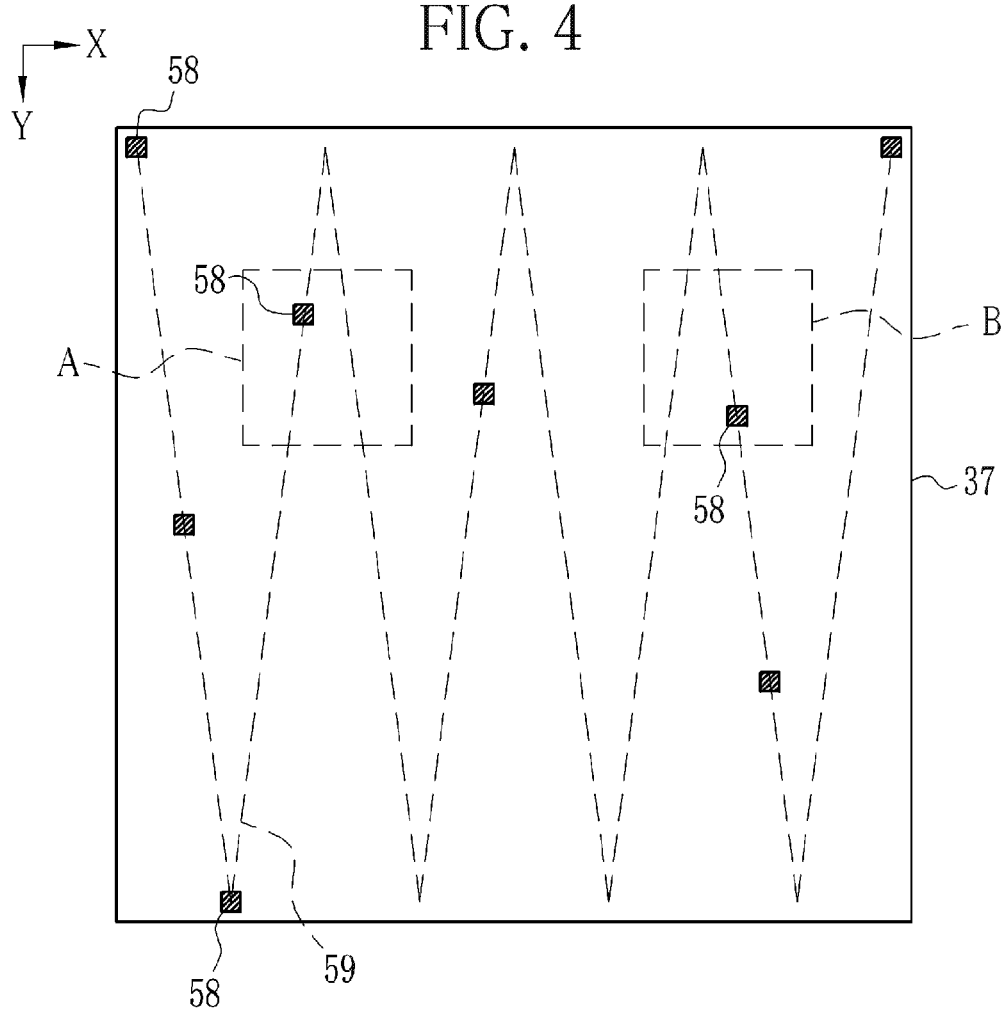
FIG. 4 is an explanatory view of the distribution of detection pixels.

As shown in FIG. 4, the detection pixels 58 are disposed along a zigzag line 59 symmetric with respect to the center of the imaging section 37, as shown by a broken line, so as to be uniformly distributed in the imaging section 37. One detection pixel 58 is laid out every two to three signal lines 41, and two or more detection pixels 58 cannot be laid out in the single signal line 41. The positions of the detection pixels 58 are known in manufacturing the FPD 35, and the FPD 35 has a nonvolatile memory (not shown) that stores in advance the positions (coordinates) of every detection pixel 58. Contrarily to this embodiment, the detection pixels 58 may be disposed in a concentrated manner. The disposition of the detection pixels 58 is appropriately changeable. In a mammography system for inspecting a breast, for example, the detection pixels 58 are preferably localized on a chest wall side.

When the gate driver 55 issues the gate pulses and the TFTs 57 are turned on, the signal charge produced in the detection pixels 58 is read out to the signal lines 41. Since the detection pixels 58 are driven by a drive source different from that of the normal pixels 36, the signal charge is read out from the detection pixel 58 even if the normal pixels 36 in the same row as the detection pixel 58 are in the charge accumulation operation, in other words, in the middle of accumulating the signal charge. The electric charge produced in the detection pixel 58 flows into the capacitor 46b of the integrating amplifier 46 in the signal line 41 connected to the detection pixel 58. While the normal pixels 36 perform the charge accumulation operation, the electric charge that is produced by the detection pixels 58 and accumulated in the integrating amplifiers 46 is outputted to the A/D 49 at a predetermined sampling rate.

The control unit 33 includes various image processing circuits (not shown) that perform offset correction, sensitivity correction, and defect correction to the X-ray image data stored in the memory 51. The X-ray image data is read out from the memory 51 on a pixel-by-pixel basis, and is applied to the offset correction and then the sensitivity correction. After that, the X-ray image data is applied to the defect correction. The corrected X-ray image data is written to the memory 51 again. In the offset correction, an offset correction image that is obtained by the FPD 35 in the absence of the X-ray emission is subtracted from the X-ray image on a pixel-by-pixel basis, to eliminate fixed pattern noise caused by the individual difference of the signal processing circuit 45 and imaging environment.

The sensitivity correction circuit, which is also called gain correction circuit, corrects sensitivity variations in the photodiode 38 among the normal pixels 36, variations in the output properties of the signal processing circuit 45, and the like. Sensitivity correction data includes a coefficient, for correcting deviation from a standard value, that is determined on a pixel-by-pixel basis so as to equalize output from each pixel, in an image in which an image after the offset correction is subtracted from an image obtained with application of a predetermined X-ray dose in the absence of the object. For example, in a case where output of a pixel B is 0.8 while output of a pixel A is 1 being the standard value, the coefficient of the pixel B becomes 1.25 (1/0.8=1.25).

The defect correction circuit performs linear interpolation of a pixel value of a defective pixel with a pixel value of an adjoining normal pixel based on defective pixel information included with shipment. A pixel value of the detection pixel 58 present within an irradiation area, which is used for dose detection in the AEC, is interpolated in a like manner.

The offset correction image and the sensitivity correction data are obtained in the shipment of the electronic cassette 11, in regular maintenance by a service staff member of a manufacturer, or at the start of each hospital day by the radiological technician, and are written to an internal memory of the control unit 33. The various image processing circuits described above may be provided in the control device 12, instead of the control unit 33.

The AEC unit 52 is controlled by the control unit 33 during the X-ray emission. The AEC unit 52 obtains digital voltage signals (hereinafter called dose detection signals) from the signal lines 41 connected to the detection pixels 58 through the A/D 49, and performs the AEC based on the obtained dose detection signals.

As shown in FIG. 5, the AEC unit 52 has an integrator 75, a comparator 76, and a threshold value generator 77. The integrator 75 integrates a mean value, a maximum value, a mode value, or a total value of the dose detection signals from the detection pixels 58 present within the irradiation area. The comparator 76 starts monitoring an integral value of the dose detection signals from the integrator 75, upon shifting from the standby mode for repeating the reset operation to the imaging mode for starting the charge accumulation operation. The comparator 76 digitally compares the integral value with an emission stop threshold value produced by the threshold value generator 77 at appropriate timing. When the integral value has reached the threshold value, the comparator 76 issues an emission stop signal. To hasten the stop of X-ray emission, the AEC unit 52 may be disposed before the A/D 49, and produce and issue the emission stop signal based on an analog signal. Alternatively, the analog signal may be transmitted to the control device 12 as the dose detection signal, and the source controller 21 of the control device 12 may produce the emission stop signal.

The wireless communicator 30 performs transmission and reception of the AEC signal, more specifically, reception of the inquiry signal, transmission of the emission permission signal in response to the inquiry signal, reception of the emission start signal, and transmission of the emission stop signal from the comparator 76 (only the emission stop signal is shown in FIG. 5).

Adhoc communication is used as a wireless communication method between the wireless communicator 25 of the control device 12 and the wireless communicator 30 of the electronic cassette 11. The ad-hoc communication establishes direct wireless communication between wireless communication units. Therefore, communication delay (lag) is hard to occur, and average delay time in the data communication becomes small, in comparison with infrastructure communication, which performs communication of various types of data including an electronic medical chart, a medical report, and accounting data among medical devices other than the X-ray imaging system 2 through a wireless access point, a hospital LAN, or a switching device such as a hub. In other words, the communication speed of the ad-hoc communication is faster than that of the infrastructure communication.

In most cases, the control device 12 is installed in the examination room. Thus, the use of the ad-hoc communication in transmitting and receiving the AEC signal, including the emission stop signal between the control device 12 and the electronic cassette 11, makes the communication stable and speedy without the occurrence of delay, because radio waves are accessible due to the short distance between the control device 12 and the electronic cassette 11. Also, eliminating the need for providing relay parts facilitates immediate return from the communication failure only by checking operation of the wireless communicators 25 and 30 and replacing a broken part.

As a wireless communication method between the wireless communicators 25 and 30, for example, a radio beacon or an optical beacon represented by infrared communication such as IrDA is preferably adopted. In the optical beacon and the radio beacon, a transmitted and received signal has a relatively low bit number, and the communication method is so simple as not to cause delay. Thus, the optical beacon or the radio beacon is preferably used in communication of the AEC signal to stop the X-ray emission as soon as the integral dose has reached the target dose.

As shown in FIG. 6, one exposure condition is settable for each body portion in the control device 12 by the input device 16. The exposure condition includes the tube voltage, the tube current, the irradiation area to be used in choosing the detection pixels 58, the emission stop threshold value for judging the stop of X-ray emission by comparison with the integral value of the dose detection signals, and the like. This information about the exposure conditions is stored in the storage device. The exposure condition that corresponds to the body portion designated by the input device 16 is read out from the storage device, and is provided for the electronic cassette 11 through the wireless communicator 25 or the wired communicator 26.

The irradiation area is the most noteworthy area in diagnosis that is specified in each body portion, and an area from which the dose detection signal is stably obtainable. One or more detection pixels 58 present within the irradiation area are used in the AEC. Referring to FIG. 4, in a case where the imaged body portion is the chest, for example, areas "A" and "B" that are enclosed by broken lines, i.e. areas of the lung fields are assigned as the irradiation areas. Each irradiation area is represented by X and Y coordinates. If the irradiation area is in a rectangular shape, as in the case of this embodiment, the X and Y coordinates of two points connected by a diagonal line are stored. The X and Y coordinates correspond to the positions of the detection pixels 58 and the normal pixels 36 in the imaging section 37. An X axis extends in a direction parallel to the scan lines 40. A Y axis extends in a direction parallel to the signal lines 41. The most upper left detection pixel 58 is assigned as an origin point (0, 0).

Figure 7:
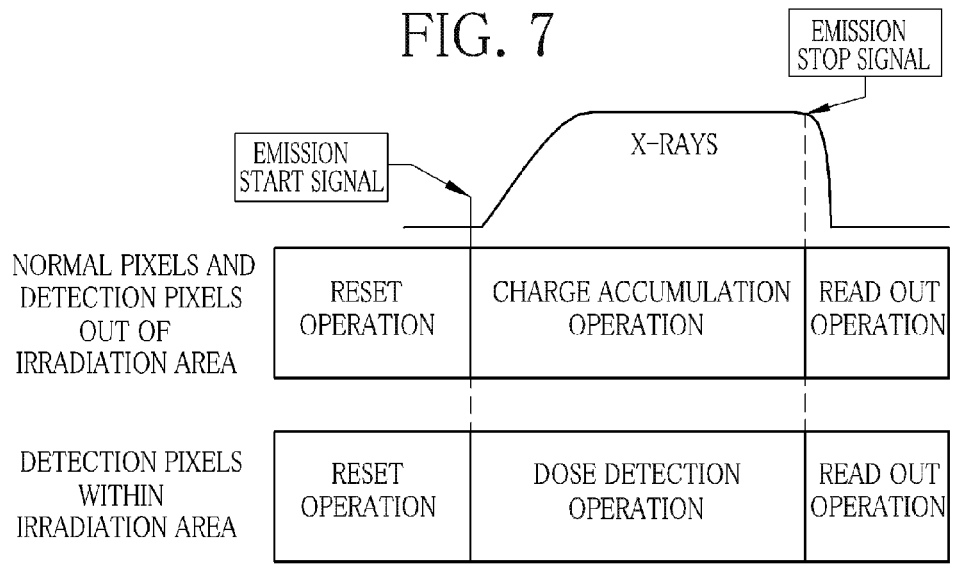
FIG. 7 is an explanatory view showing an operation flow of an FPD in X-ray imaging.

In FIG. 7, the FPD 35 is in the standby mode before the start of imaging. In this mode, the gate drivers 42 and 55 are operated in synchronization with each other, and repeatedly perform the reset operation in which both the normal pixels 36 and the detection pixels 58 are reset together from row to row. Upon receiving the emission start signal by the wireless communicator 30, the control unit 33 shifts the FPD 35 from the standby mode to the imaging mode, so the FPD 35 starts the charge accumulation operation. At the same time, the gate driver 55 keeps turning on the TFT 57 of every detection pixel 58 to start dose detection operation in which the dose detection signal is continuously outputted.

The comparator 76 of the AEC unit 52 starts monitoring the integral value of the dose detection signals from the integrator 75. After that, when the integral value of the dose detection signals has reached the emission stop threshold value, the comparator 76 issues the emission stop signal. The emission stop signal is transmitted from the wireless communicator 30 and received by the wireless communicator 25, so the X-ray emission from the X-ray source 10 is stopped. At this time, the control unit 33 shifts every pixel, including the normal pixels 36, the detection pixels 58 present out of the irradiation area, and the detection pixels 58 present within the irradiation area, from the charge accumulation operation to the readout operation. In the readout operation, the gate drivers 42 and 55 synchronize with each other, and turn on the TFTs 39 and 57 from row to row to sequentially read out the electric charge from every pixel on a row-by-row basis. Then single imaging operation is completed, and the FPD 35 returns to the standby mode. The pixel values of the detection pixels 58 present within the irradiation area that are obtained in the readout operation are not used in producing the image data, and pixel values interpolated by the defect correction circuit are used instead. This is because the FPD 35 of this embodiment adopts a TFT method of a destructive read type, so the detection pixels 58 present within the irradiation area need the defect correct as with the defective pixels. However, in the case of adopting a CMOS method or the like of a nondestructive read type, the electric charge accumulated in every pixel including the detection pixels 58 is usable for production of the image, so the defect correction is not de rigueur.

Figure 8:
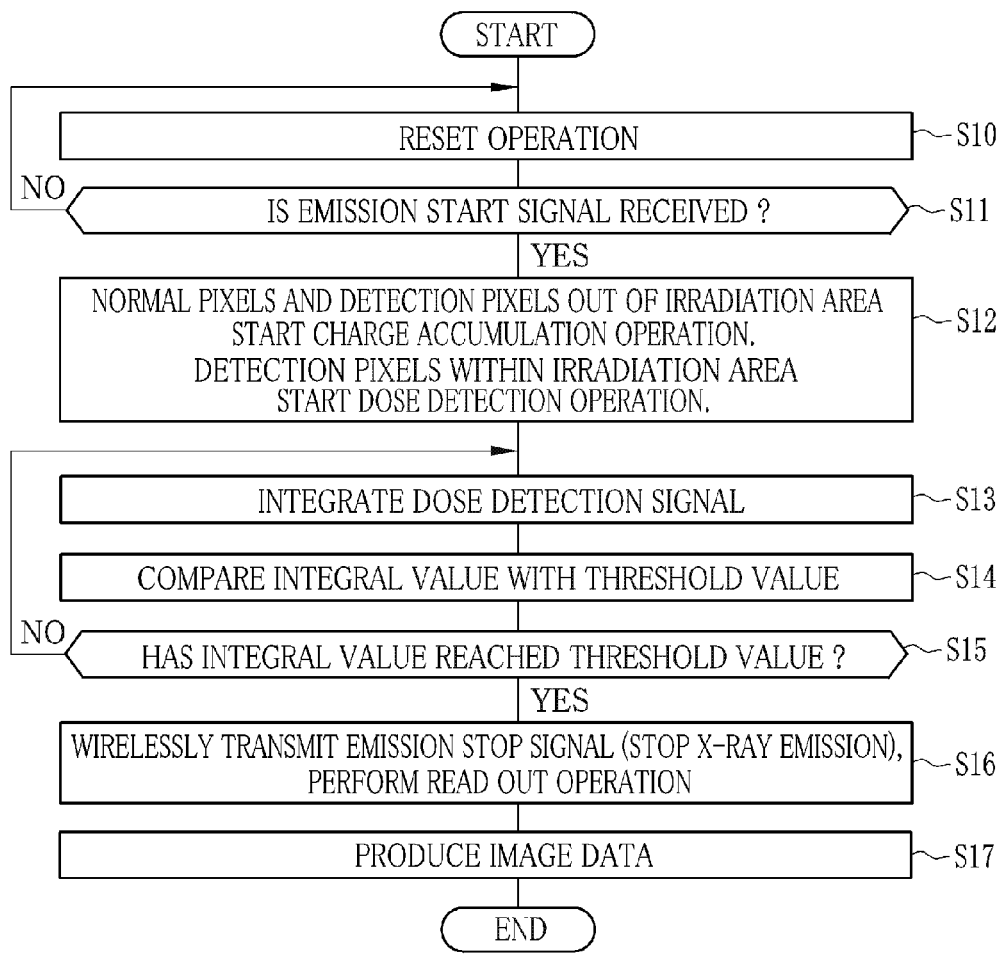
FIG. 8 is a flowchart of an X-ray imaging process.

Next, the operation of the X-ray imaging system 2 will be described with referring to a flowchart of FIG. 8. The radiological technician makes the patient stand up at a predetermined position in front of the imaging stand 13 or lie down on the imaging table 14. The height and horizontal position of the electronic cassette 11, which is mounted on the imaging stand 13 or the imaging table 14 being used, are adjusted with respect to the position of the body portion to be imaged. In accordance with the position of the electronic cassette 11 and the size of the body portion, the height and horizontal position of the X-ray source 10 and the size of the irradiation field are adjusted. The exposure condition is set in the control device 12.

In S10, the FPD 35 repeats the reset operation in the standby mode before the start of X-ray imaging. Upon the half press of the emission switch 15, the inquiry signal and the emission permission signal are transmitted and received between the wireless communicators 25 and 30. Upon the full press of the emission switch 15, the control device 12 issues the emission start signal. When the wireless communicator 30 receives the emission start signal (YES in S11), the normal pixels 36 and the detection pixels 58 present out of the irradiation area are shifted from the reset operation to the charge accumulation operation by the gate drivers 42 and 55, namely, the X-ray imaging system 2 turns into the imaging mode. On the other hand, the gate driver 55 keeps turning on the TFTs 57 of the detection pixels 58 present within the irradiation area. The detection pixels 58 present within the irradiation area are shifted to the dose detection operation (S12).

Upon the full press of the emission switch 15, the X-ray source 10 starts the X-ray emission. The normal pixels 36 and the detection pixels 58 present out of the irradiation area accumulate the electric charge produced by the X-ray emission. The electric charge produced in the detection pixels 58 present within the irradiation area flows into the integrating amplifiers 46 through the signal lines 41, and is integrated. The integral signals are transmitted as the dose detection signals to the A/D 49 through the amplifiers 50, the CDSs 47, and the MUX 48. The A/D 49 converts each dose detection signal into a digital signal at the predetermined sampling rate, and transmits the digital dose detection signals to the AEC unit 52.

In the AEC unit 52, the integrator 75 integrates the dose detection signals (S13). The threshold value generator 77 issues the emission stop threshold value provided by the control device 12, and outputs the emission stop threshold value to the comparator 76. The comparator 76 compares the integral value of the dose detection signals from the integrator 75 with the emission stop threshold value from the threshold value generator 77 (S14). When the integral value of the dose detection signals has reached the emission stop threshold value (YES in S15), the comparator 76 issues the emission stop signal. This emission stop signal is wirelessly transmitted through the wireless communicator 30 to the wireless communicator 25 of the control device 12. The FPD 35 is shifted from the charge accumulation operation to the readout operation (S16), and the X-ray image data is written to the memory 51.

Upon receiving the emission stop signal by the wireless communicator 25, the source controller 21 stops the electric power supply from the high voltage generator 23 to the X-ray source 10 in the control device 12. Thus, the X-ray emission is stopped.

The control unit 33 of the electronic cassette 11 applies various types of image processing to the X-ray image data outputted to the memory 51 to produce the X-ray image of a single frame. The processed X-ray image data is written to the memory 51 again (S17). After that, the X-ray image data is read out from the memory 51, and is wiredly or wirelessly transmitted to the control device 12 through the wired communicator 26 or the wireless communicator 25, and is written to the memory 24. The X-ray image data stored in the memory 24 is displayed on the monitor 17 as the X-ray image for use in diagnosis.

Even if the control device 12 and the electronic cassette 11 are connected with the cable, the AEC signal including the emission stop signal is always transmitted wirelessly. In case where the communication failure occurs in the wired communication, it is necessary to check a cable break, a connector contact failure, a breakdown in a relay device such as a hub if there is the relay device between the control device 12 and the electronic cassette 11 in order to find out a cause. However, in the wireless communication, it is possible to simply identify the cause of communication failure only by the operation check of the wireless communicators 25 and 30, and quickly recover from the communication failure. Therefore, the wireless communication facilitates preventing long downtime, in other words, prevents the patient from waiting for long time.

Even if the X-ray image data cannot be transmitted from the electronic cassette 11 to the control device 12, the X-ray image data is stored in the memory 51 of the electronic cassette 11. Thus, the X-ray imaging is continued, only if the wireless communication function of the AEC signal is alive. Providing the memory 51 having a capacity large enough for tomosynthesis imaging, in which imaging is continuously performed a plurality of times, makes it possible to complete the continuous imaging without being interrupted, even in case where the image data cannot be transmitted.

The AEC signal, being an ON/OFF signal, has a data size much smaller than that of the image data. Thus, the wireless communication requires less power (low radio field intensity), and hence is available to the patient having a pacemaker without any problems. The wireless communication requires less power consumption. Since the image data has a large data size, transmitting the image data through the wireless communication requires much power consumption. However, when the cable is connected, a communication method of the image data is switched to the wired communication to reduce the power consumption.

Transmitting and receiving the AEC signal between the control device 12 and the electronic cassette 11 through the ad-hoc communication eliminates the need for providing an additional device such as the hub therebetween, and hence allows quick investigation into the cause of the communication failure and quick recovery therefrom. Adopting the beacon, which has simple structure and ease of failure analysis, produces the same effect.

Figure 9A:
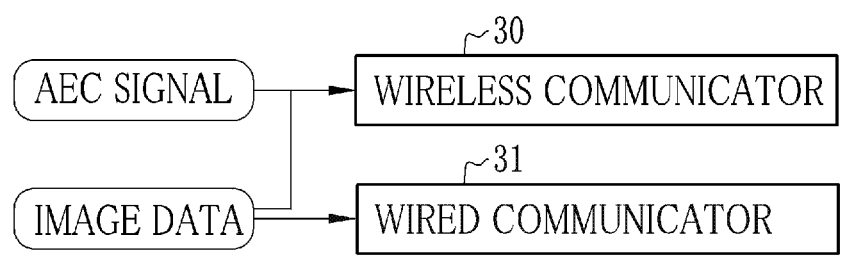
FIG. 9A is an explanatory view showing an example of communication resources of an AEC signal and image data.
Figure 9B:
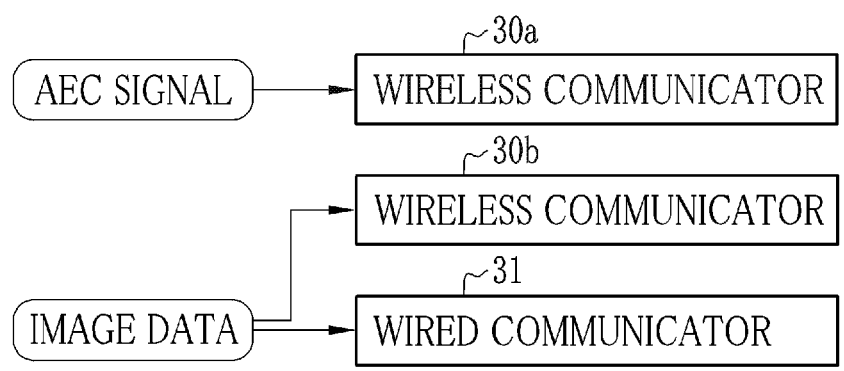
FIG. 9B is an explanatory view showing another example of communication resources of the AEC signal and the image data.

The AEC signal and the other signals including the image data may be transmitted through the same wireless communication resource as shown in FIG. 9A, or through the different wireless communication resources (wireless communicators 30a and 30b) as shown in FIG. 9B. In the case of using the same resource, the number of component parts is reduced. In the case of using the different resources, there is no need for concern about overlap in transmission and reception timing of the AEC signal and the other signals.

In the above embodiment, the AEC signal includes the inquiry signal, the emission permission signal issued in response to the inquiry signal, the emission start signal, and the emission stop signal. However, the AEC signal may denote only the emission stop signal. In this case, when the electronic cassette 11 and the control device 12 are connected through the cable, only the emission stop signal is transmitted and received wirelessly, while the inquiry signal, the emission permission signal, the emission start signal, and the image data are transmitted and received wiredly. This facilitates minimizing electric power consumption of the battery. In case of a failure in the wired communication, the emission start signal cannot be transmitted. Thus, the electronic cassette 11 detects and judges the start of X-ray emission using the detection pixels 58, and shifts from the reset operation to the charge accumulation operation. The X-ray imaging can be started by detection of the X-rays as described above, but communication is necessarily required to stop the imaging. For this reason, by transmitting only the emission stop signal wirelessly, the X-ray imaging can be continuously performed even if the wired communication fails. Also, in case of the failure in the wireless communication, quick failure analysis and quick recovery can be performed.

In the above embodiment, the cable connection owing to the low battery power or the like triggers switching from the wireless communication to the wired communication between the electronic cassette and the control device. However, as shown in FIG. 10, when the electronic cassette is loaded into the holder of the imaging stand or table, the wireless communication may be switched to the wired communication automatically.

Figure 10:
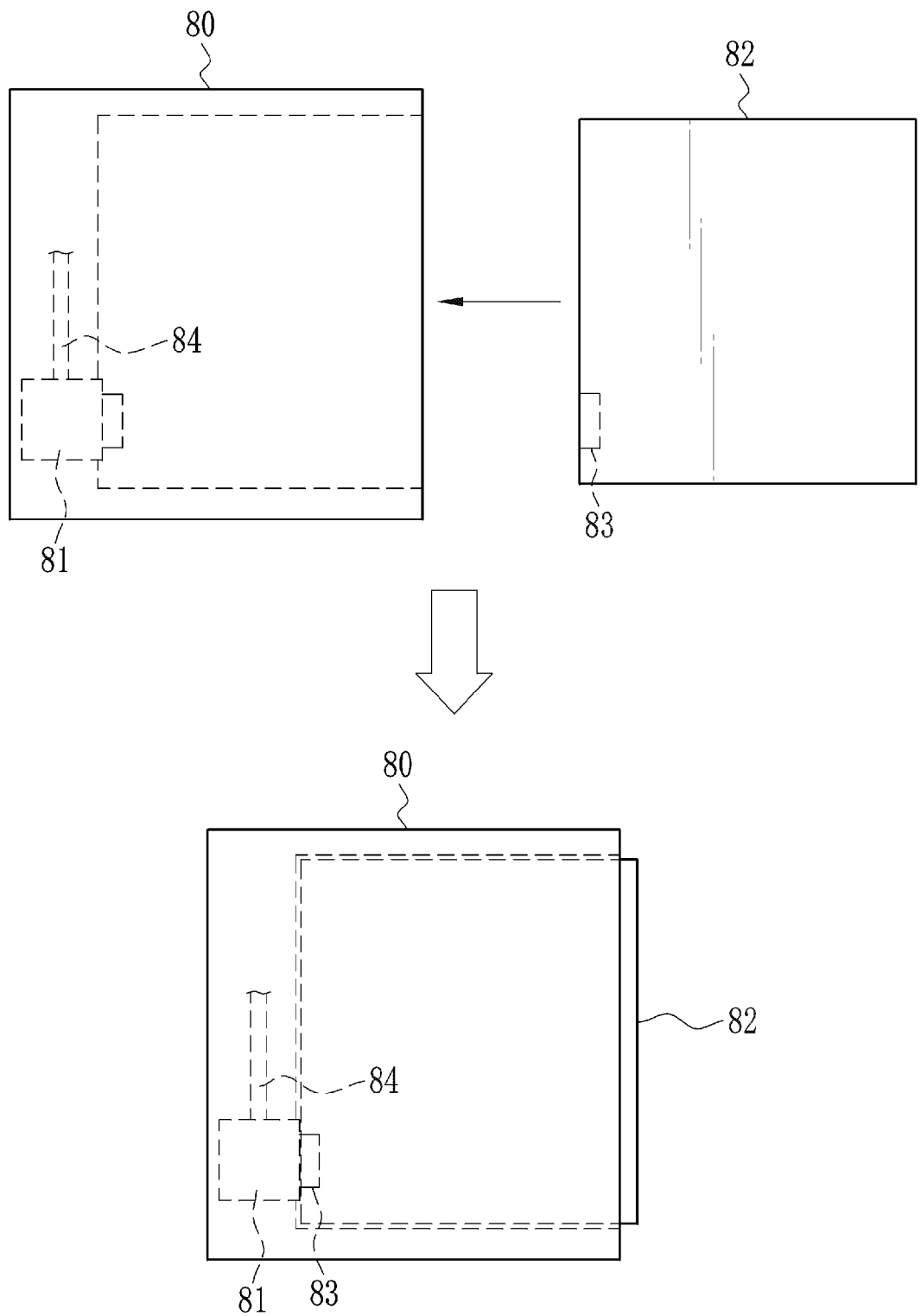
FIG. 10 is an explanatory view showing a state of loading the electronic cassette into a holder of an imaging stand.

As shown in FIG. 10, a holder 80 is provided with a connector 81. When an electronic cassette 82 is set in the holder 80, the connector 81 is inserted into a socket 83 provided on a side surface of the electronic cassette 82. A cable 84 extending from the connector 81 is drawn out to the outside from a lower portion of the imaging stand or table through the interior of the imaging stand or table. Thus, by eliminating the need for connecting the cable to the electronic cassette, operability and convenience are further improved.

Figure 11:
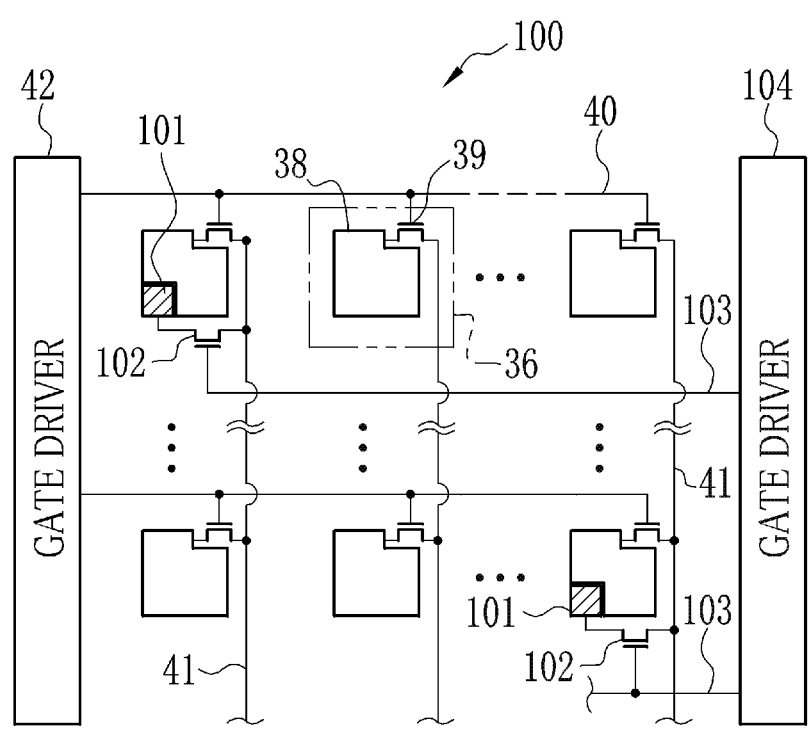
FIG. 11 is a block diagram of an FPD of another embodiment.

The normal pixel 36 and the detection pixel 58 have the same size and structure in the above embodiment. However, in an FPD 100 shown in FIG. 11, a part of the photodiode 38 of the normal pixel 36 is divided as a detection pixel 101. To the detection pixel 101, a TFT 102, a scan line 103, and a gate driver 104 are connected, aside from the TFT 39, the scan line 40, and the gate driver 42 of the normal pixel 36. Just as with the above embodiment, the accumulated electric charge is read out from the detection pixels 101 through the signal lines 41 independently of the normal pixels 36. In the readout operation, however, the gate pulses are simultaneously inputted to the scan lines 40 and 103 of the row having the detection pixel 101 present out of the irradiation area, to read out the accumulated electric charge at the same timing from both the normal pixels 36 and the detection pixel 101. Thus, an image signal that is composed of a mixture of the electric charge accumulated in the normal pixel 36 and the detection pixel 101 is obtained. This image signal is almost the same as an image signal obtained from the normal pixel 36 without having the detection pixel 101. On the other hand, in the row having the detection pixel 101 present within the irradiation area, an image signal is read out only from the normal pixel 36. This image signal is interpolated based on a ratio in size and output between the normal pixel 36 and the detection pixel 101.

The detection pixels each having the photodiode that is directly connected to the signal line without through the TFT may be provided instead. In this case, the electric charge produced in the detection pixels keeps flowing into the signal processing circuit through the signal lines, regardless of the operation of the gate driver. In this case, the AEC unit 52 chooses one or more detection pixels present within the irradiation area, and integrates signals therefrom at the integrator 75.

With taking advantage of the fact that electric current flowing through the bias line is in proportional to the amount of the electric charge produced in the pixel, the electric current flowing through the bias line connected to the specific pixel may be monitored to detect the received X-ray dose. In further another case, the received X-ray dose may be detected based on leak charge from the pixel in a state where all the TFTs are turned off. Furthermore, another AEC detection pixel that is independent of the normal pixels may be provided coplanarly to the imaging section having the normal pixels. In further another case, the dose detection sensor composed of a well-known ion chamber (ionization chamber) and the like may be used independently of the electronic cassette.

In the above embodiment, the emission stop signal is issued when the integral value of the dose detection signals has reached the emission stop threshold value. Instead of this, time for the integral value to reach the emission stop threshold value may be predicted. The emission stop signal may be issued, when the predicted time has elapsed. In this case, the integral value of the dose detection signals is taken out at the start of the X-ray emission after a lapse of predetermined time. An integral value per time is calculated from this integral value, and the emission stop threshold value is divided by the integral value per time to calculate the emission time (predicted time).

The electronic cassette 11 may keep on transmitting an emission continuation signal from its wireless communicator 30 to the wireless communicator 25 of the control device 12, from the start of X-ray emission till the AEC unit 52 judges that the integral value of the received X-ray dose has reached the target dose. When the reception of the emission continuation signal by the wireless communicator 25 is stopped, the X-ray emission may be stopped. In the case of using the emission stop signal, if the transmission and reception of the emission stop signal fail between the electronic cassette and the control device, the X-ray emission cannot be stopped. However, in the case of using the emission continuation signal, if the transmission and reception of the emission continuation signal fail, the X-ray emission is stopped, thereby assuring safety.

The control device 12 and the electronic cassette 11 are separate in the above embodiment, but the electronic cassette 11 may have the function of the control device 12. The source controller 21 and the cassette controller 22 of the control device 12 may be separated into different devices. The present invention may be applied to an X-ray image detecting device fixed on the imaging stand or table, in addition to the portable electronic cassette.

The present invention is applicable to a radiation imaging system using another type of radiation such as γ-rays instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation image detecting device for detecting a radiographic image, said radiation image detecting device making communication with a control device for controlling a radiation source, said radiation image detecting device comprising:
    an imaging section having pixels arranged in two dimensions, each of said pixels converting radiation emitted from said radiation source into electric charge and accumulating said electric charge, said radiographic image being obtained by reading out said electric charge from said pixels;
    a dose detection sensor for detecting a received dose of said radiation;
    an automatic exposure control unit for issuing an emission continuation signal for commanding continuation of radiation emission or an emission stop signal for commanding stop of said radiation emission based on a dose detection signal from said dose detection sensor;
    a wired communicator for transmitting and receiving a signal to and from said control device in a wired manner, said wired communicator being actuated in response to cable connection between said control device and said radiation image detecting device; and
    a wireless communicator for transmitting and receiving said signal to and from said control device in a wireless manner, said wireless communicator being in charge of transmission of at least said emission continuation signal or said emission stop signal regardless of presence or absence of said cable connection.

2. The radiation image detecting device according to claim 1, wherein said wired communicator transmits said radiographic image to said control device through a cable.

3. The radiation image detecting device according to claim 2 further comprising a memory, wherein if communication failure occurs between said wired communicator and said control device, said memory stores said radiographic image to be transmitted to said control device.

4. The radiation image detecting device according to claim 3, wherein when said wired communicator receives an emission start signal of said radiation from said control device through said cable, each of said pixels starts accumulating said electric charge.

5. The radiation image detecting device according to claim 3 further comprising a control unit, said control unit performing the steps of:
    if said communication failure occurs between said wired communicator and said control device connected each other through said cable, judging start of said radiation emission from said radiation source based on said dose detection signal from said dose detection sensor; and
    upon judgment of said start of said radiation emission, making each of said pixels start accumulating said electric charge.

6. The radiation image detecting device according to claim 1, wherein said wireless communicator transmits and receives said signal through ad-hoc communication.

7. The radiation image detecting device according to claim 1, wherein said wireless communicator transmits and receives said signal through a beacon.

8. The radiation image detecting device according to claim 1, wherein said dose detection sensor is arranged together with said pixels in two dimensions.

9. An electronic cassette comprising:
    said radiation image detecting device according to claim 1; and a portable housing containing said radiation image detecting device.

10. The electronic cassette according to claim 9, wherein when said electronic cassette is loaded in an imaging stand, said wired communicator is connected to said control device through a cable extending through an interior of said imaging stand.

11. A radiation imaging system comprising:
A. a radiation source for emitting radiation to an object;
B. a control device for controlling said radiation source and a radiation image detecting device, said control device having a first wired communicator and a first wireless communicator;
C. said radiation image detecting device including:
an imaging section having pixels arranged in two dimensions, each of said pixels converting said radiation emitted from said radiation source into electric charge and accumulating said electric charge, a radiographic image being obtained by reading out said electric charge from said pixels;
a dose detection sensor for detecting a received dose of said radiation;
an automatic exposure control unit for issuing an emission continuation signal for commanding continuation of radiation emission or an emission stop signal for commanding stop of said radiation emission based on a dose detection signal from said dose detection sensor;
a second wired communicator being actuated when being connected to said first wired communicator through a cable, for performing transmission and reception of a signal in a wired manner; and
a second wireless communicator for transmitting and receiving said signal to and from said first wireless communicator in a wireless manner, said second wireless communicator being in charge of transmission of at least said emission continuation signal or said emission stop signal regardless of presence or absence of connection of said cable.

* * * * *